(12) United States Patent
Hoogenakker et al.

(10) Patent No.: US 7,682,336 B2
(45) Date of Patent: Mar. 23, 2010

(54) GAS ASSISTED ENDOSCOPIC APPLICATOR SYSTEM

(75) Inventors: Jon E. Hoogenakker, Inver Grove Heights, MN (US); Bradley D. Robb, Maple Plain, MN (US)

(73) Assignee: Micromedics, Inc., St. Paul, MN (US)

( * ) Notice: Subject to any disclaimer, the term of this patent is extended or adjusted under 35 U.S.C. 154(b) by 1260 days.

(21) Appl. No.: 11/128,958

(22) Filed: May 13, 2005

(65) Prior Publication Data

US 2007/0005007 A1     Jan. 4, 2007

(51) Int. Cl.
*A61M 1/00* (2006.01)
*A61M 3/00* (2006.01)
*A61M 37/00* (2006.01)

(52) U.S. Cl. .................. 604/146; 604/140; 604/82; 604/45

(58) Field of Classification Search .................. 604/45, 604/82, 191, 140, 146; 137/625.66; 433/101
See application file for complete search history.

(56) References Cited

U.S. PATENT DOCUMENTS

| | | | |
|---|---|---|---|
| 4,040,420 A | 8/1977 | Speer | |
| 4,359,049 A | 11/1982 | Redl et al. | |
| 4,733,666 A | 3/1988 | Mercer, Jr. | |
| 4,826,048 A | 5/1989 | Skorka et al. | |
| 4,874,368 A | 10/1989 | Miller et al. | |
| 4,902,281 A | 2/1990 | Avoy | |
| 4,978,336 A | 12/1990 | Capozzi et al. | |
| 5,368,563 A | 11/1994 | Lonneman et al. | |
| 5,474,540 A * | 12/1995 | Miller et al. ................. | 604/191 |
| 5,779,662 A * | 7/1998 | Berman ....................... | 604/22 |
| 6,478,808 B2 | 11/2002 | Nowakowski et al. | |
| 2002/0165483 A1* | 11/2002 | Miller et al. .................. | 604/82 |
| 2006/0116630 A1* | 6/2006 | Garabet ....................... | 604/65 |

* cited by examiner

*Primary Examiner*—Nicholas D Lucchesi
*Assistant Examiner*—Rebecca E Eisenberg
(74) *Attorney, Agent, or Firm*—Westman, Champlin & Kelly, P.A.

(57) ABSTRACT

An apparatus for making and administering two non-homogenous liquids to target tissue includes a spray comprising two syringes for containing the first and second non-homogenous liquid where the syringes are adapted to be removably coupled to an applicator. The applicator includes a pair of elongated tubes each having a tubular sheath at a proximal end, a distal end and a lumen in which the pair of elongated tubes are disposed. The apparatus includes a regulator module having an inlet port adapted for connection to a source of gas under pressure and a gas outlet port adopted for connection to the gas inlet port of the sheet. A vent gas inlet port is adapted for connection to a vent port of an endoscopic cannula where the regulator vents a quantity of gas from the endoscopic cannula approximately equal to a quantity of gas introduced at the gas inlet port of the sheet.

16 Claims, 5 Drawing Sheets

GAS ASSISTED ENDOSCOPIC APPLICATOR SYSTEM

BACKGROUND OF THE INVENTION

I. Field of the Invention

This invention relates generally to endoscopic application of bio-materials to target tissue in the course of a laparoscopic surgical procedure, and more particularly to an endoscopic spray applicator system design to mix two non-homogeneous liquids and to allow the resulting mixture to be applied thinly and evenly by spraying, on a difficult to reach treatment site, such as subcutaneously or within the body through an endoscopic cannula.

II. Discussion of the Prior Art

Tissue adhesives have long been recognized for their potential to hasten wound healing, reduce post-operative complications and decrease the need for drains following surgery. Typically, such adhesives have been prepared on the day of surgery from the patient's own blood. A quantity of blood would be drawn from the patient just prior to surgery and in a centrifugation process, natural clotting factors are isolated and concentrated for application on to the surgical wound while the remaining red blood cells were then reinjected or autotransfused back into the patient's bloodstream.

Fibrin sealant is a tissue adhesive that mimics the body's own natural clotting mechanism. Two basic components make up fibrin sealant, namely, fibrinogen and thrombin. Because fibrin sealant is derived from blood products, it is associated with viral disease transmission. To reduce the risk of viral-disease transmission from pooled plasma sources of fibrinogen, various viral inactivation methods are employed in commercial fibrin sealants. Blood banks often produce fibrinogen from screened, single-donor sources or use autologous fibrinogen. Currently, bovine thrombin is most often used, although methods for producing human thrombin or recombinant thrombin are being developed. Fibrin sealants can be used in a variety of surgical applications to enhance hemostasis, to seal tissues, to close fistulas and to deliver biologics or drugs.

When fibrin and thrombin are made to mix, a coagulum is formed where the platelets interdigitate with the forming fibrin web, developing a gel with adhesiveness and strength materially greater than the plasma alone. Because of the rapid clotting propensity, it is necessary to keep the two liquid constituents separated and only mixed at the distal end of the applicator. Numerous tissue adhesive applicators have been developed, such as those described in U.S. Pat. No. 4,040,420 to Speer, U.S. Pat. No. 4,359,049 to Redl, U.S. Pat. No. 4,733,666 to Eibl, U.S. Pat. No. 4,826,048 to Skorka, U.S. Pat. No. 4,874,368 to Miller, U.S. Pat. No. 4,902,281 to Avoy, U.S. Pat. No. 4,978,336 to Capozzi, U.S. Pat. No. 5,368,563 to Lonnemann and U.S. Pat. No. 5,474,540 to Miller. A variety of these types of applicators exist including internal swirl or mixing chamber applicators and external combining applicators, such as external swirl applicators and external spray or stream overlapping applicators.

The Skorka '048 patent, the Capozzi '336 and '315 patents concerns swirl or other pre-ejection mixing applicators where mixing is performed by squirting or otherwise forcing the two non-homogeneous fluids into a swirl or other mixing chamber where the fluids mix to some degree based upon turbulence in the swirl chamber and the material properties and are thereafter ejected from the applicator. The mixing occurs inside the applicator and, thus, time is critical, as it must be ejected prior to coagulation. In certain applications, such as where one or more of the solutions or fluids is thick or high viscous, internal swirling results in only marginal or partial mixing, while in other applications, such as where all of the solutions or fluids are thin or not highly viscous, substantial and effective mixing occurs.

In contrast, the applicators described in the Speer '420, the Miller '368 and the Avoy '281, the Lonnemann '563 and the Miller '540 patents are external combining applicators. Here, the two solutions are brought into contact with one another at the point of use or functional tissue adhesive creation. External combining eliminates premature mixing problems. However, with many external combining applicators, thorough mixing of the solutions does not occur and, instead, only adjacent portions of the solutions mix or combine well large percentages remain unmixed or uncombined. This results in inefficient and somewhat uncontrolled coagulation. The Lonnemann '563 patent owned by applicant's assignee is considered to be a significant advance in external combining applicators. It provides an external swirling pattern where the two fluids overlap one another resulting in improved fluid mixing.

In copending application Ser. No. 10/863,631, filed Jun. 8, 2004, and entitled "Spray Applicator", there is described a medical fluid delivery system which expels two liquid components, at least one of which is reactive, from separate syringes while simultaneously releasing a pressurized fluid, such as a compressed gas, around, adjacent to or proximate the reactive components resulting in thorough mixing of the reactive components as well as propulsion thereof in a commingled stream onto a surgical site. The teachings of such application are hereby incorporated by reference. The teachings of that application, however, do not address a further problem where such a gas propelled stream of reactive liquids, such as fibrin and thrombin are to be used in a laparoscopic procedure.

In laparoscopic procedures, a series of holes are surgically created in the abdominal wall with one to accommodate a camera and others to accommodate a cannula through which a working instrument, such as a laparoscopic scissors, forceps are inserted for grasping and cutting target tissue. It is common practice to insufflate the abdominal cavity by introducing a gas through one of the trocars, thereby expand the abdominal cavity to aid in viewing and manipulating internal organ structures. The trocars include a self-closing seal for preventing loss of insufflation gas while allowing penetration by the surgical instruments employed. The pressure employed in insufflating is generally about 15 mmHg and the introduction of additional gas by way of a laparoscopic spray applicator could result in over-inflation and distension of the abdominal wall. Means must, therefore, be provided to insure that this does not occur.

SUMMARY OF THE INVENTION

The present invention provides an apparatus for mixing and administering two non-homogeneous liquids to target tissue in an endoscopic procedure where the apparatus includes a spray set comprising a pair of syringes for containing the first and second liquids where the syringes are adapted to be removably coupled to an applicator. The applicator includes a pair of elongated tubes, each having a proximal end for attachment to the two syringes and a distal end. The pair of elongated tubes is, in turn, contained within the lumen of a tubular sheath that also has a proximal end and distal end. Affixed to the distal end of the elongated tubes and the sheath is a replaceable spray tip. The sheath also has a gas inlet port at its proximal end that is in fluid communication with the sheath lumen.

The spray set is used in combination with a regulator module. The regulator module has a regulator input port adapted for connection to a source of gas under relatively high pressure, a gas outlet port adapted for connection to the gas inlet port of the sheath and a vent gas inlet port adapted for connection to a vent port of an endoscopic cannula. The regulator module is operative to vent a quantity of gas from the endoscopic cannula approximately equal to the quantity of gas introduced through the gas inlet port of the sheath to thereby preclude the buildup of pressure within the abdominal cavity during spray application of the two non-homogeneous liquids to target tissue within the abdominal cavity.

DESCRIPTION OF THE DRAWINGS

The foregoing features, objects and advantages of the present invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
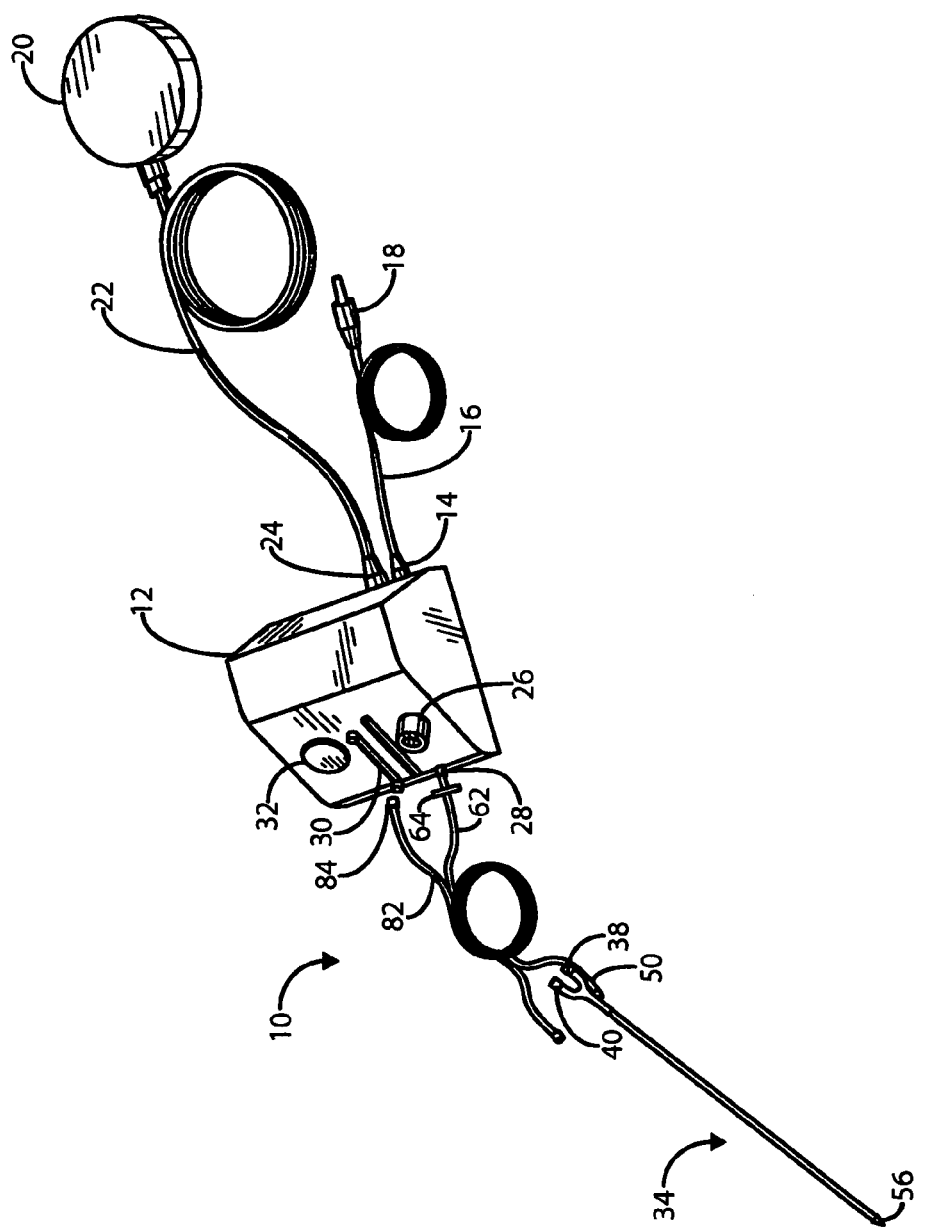
FIG. 1 is a perspective view of the gas-assisted endoscopic tissue adhesion applicator system of the present invention.

Referring to FIG. 1, there is indicated generally by numeral 10 a gas-assisted endoscopic tissue adhesive applicator system. It is seen to include a regulator module 12 having an input port 14 that is adapted to be connected by a length of tubing 16 to a source of gas under pressure. In most operating room settings, sterile pressurized gas is available at a wall outlet to which the connector 18 may be joined. Typically, the gas pressure available at the wall outlet may be in excess of 100 psi. Also connected to the regulator module 12 is a pneumatic control valve, here shown as a foot actuated valve 20. It is connected through a pneumatic line 22 to port 24.

As will be explained in greater detail herein below, a manually rotatable knob 26 is mounted on a front face of the regulator module 12 and may be used to adjust the rate of flow in liters-per-minute of gas exiting the gas outlet port 28 of the regulator module 12. While flow may be adjustable from 0-10 liters/minute, a typical range for the spray applicator may be from 1-2 liters/minute. Disposed alongside the adjustment knob 26 is a flow indicator 30 of a conventional design incorporating a pith ball within a transparent tube having scale markings associated therewith where the height of the ball within the tube is an indication of the flow rate setting.

Also visible on the front face of the regulator module 12 is a pressure gauge 32, allowing the user to monitor to assure that the air pressure maintained by the regulator is within desired limits.

Figure 2:
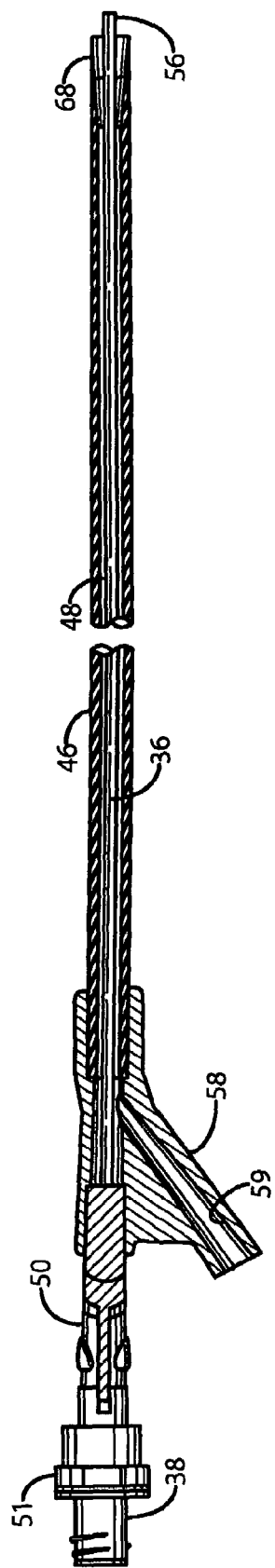
FIG. 2 is a cross-sectional view of the spray set used in the system of FIG. 1.
Figure 4:
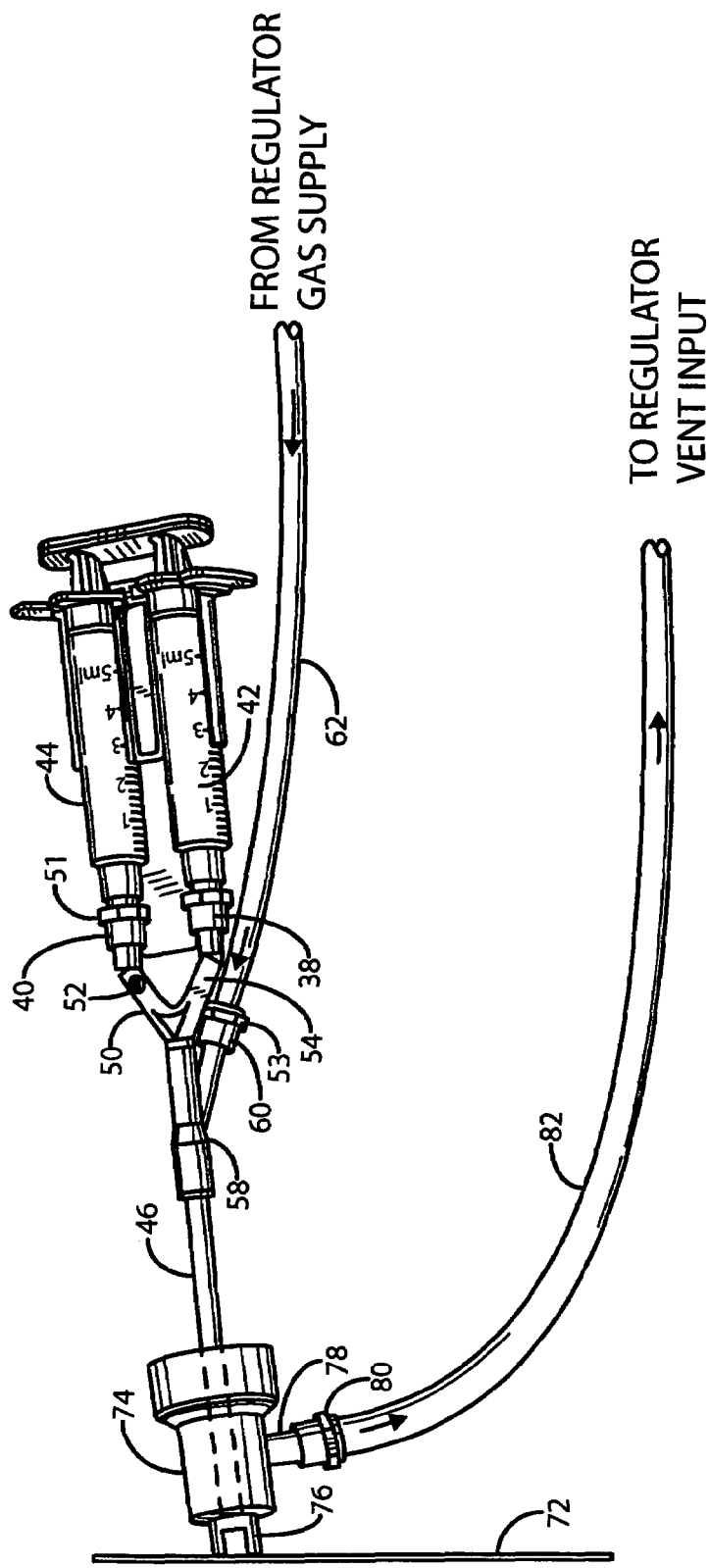
FIG. 4 is a partial isometric view of the spray set with liquid dispensing syringes attached used in combination with a trocar during an endoscopic procedure.

The system 10 further includes a spray set indicated generally by numeral 34. Referring to FIG. 2, it is seen to include a pair of elongated tubes disposed in close, side-by-side relationship and of which only tube 36 is seen in the cross-sectional view of FIG. 2. The proximal end of the pair of tubes are joined to Luer fittings 38 and 40 allowing attachment of the spray set 34 to a pair of hypodermic syringes 42 and 44 (FIG. 4). The two syringes may be of differing volumes to accommodate a desired ratio of the liquids to be combined.

The pair of elongated tubes, as at 36, is preferably hypodermic stock and may be of the same internal diameter or, alternatively, may also be of a differing diameter. The elongated tubes, as at 36, are preferably welded to one another and are surrounded by a tubular sheath 46 with a clearance space 48 therebetween. The sheath may be of stainless steel or other suitable material. The distal ends of the pair of tubes 36 are designed to extend beyond the distal end of the surrounding sheath 46. The Luer fittings 38 and 40 are mounted on a molded plastic hub 50 along with check valves 51 and 53. The check valves serve to prevent back flow into the syringes. The bifurcated legs 52 and 54 (FIG. 4) each include a central bore in fluid communication with the outlets of the syringes 42 and 44 and they individually lead to the pair of elongated tubes of hypodermic stock. As such, liquid ejected from the syringe 42 remains separated from the liquid ejected from syringe 44 and do not mix with one another until reaching the distal tip 56 of the spray set. Because the distal ends of the pair of hypo-tubes 36 extend beyond the distal end of the sheath, cleaning of the spray set is facilitated.

Affixed to the outer sheath 46 of the spray set is a Y-connector 58 (FIGS. 2 and 4) which also includes a Luer fitting 60 for accommodating attachment of a length of plastic tubing 62 that is adapted to be connected to the gas outlet port 28 of the regulator module 12. Thus, air under pressure can be made to flow from the outlet port 28 through a filter device 64 and the tubing 62 and thence through the Y-connector 58 and the lumen 48 of the sheath 46 to reach the distal end of the spray set.

Figure 3:
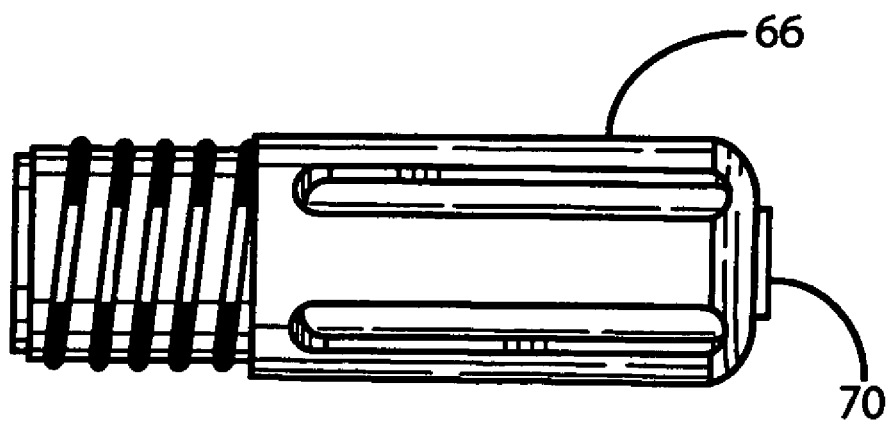
FIG. 3 is an enlarged view of the replaceable spray tip used with the spray set of FIG. 2.

Referring next to FIG. 3, there is illustrated a replaceable spray tip 66 that is adapted to be removably attached to the distal end 68 of the sheath 46 by means of a threaded coupling. The interior of the spray tip 66 is designed to blend the two liquid made to flow through the elongated hypodermic stock tubes 36 with air or other suitable gas coming through the regulator to create a vortex generating an aerosol-like spray or mist exiting the tip opening 70 of the replaceable spray tip 66. The replaceable tips are preferably made from a radiopaque polymer.

Turning momentarily again to FIG. 4, the line 72 represents the abdominal wall of a patient undergoing endoscopic surgery. The spray set 34 is shown as having the sheath 46 inserted through an insufflation seal 74 affixed to the end of a trocar 76 that is shown as penetrating through the abdominal wall 72. The seal 74 is adapted to prevent escape of insufflation gas that is delivered through a trocar to expand the abdomen and provide better access to internal organs being operated upon.

In accordance with the present invention, the trocar 76, and especially the seal fitting 74, has a gas exit port 78 with a Luer fitting 80 allowing a length of plastic tubing 82 to be affixed thereto. As shown in FIG. 1, the tubing 82 is adapted to be connected to the regulator module 12 at a vent gas inlet port 84.

Figure 5:
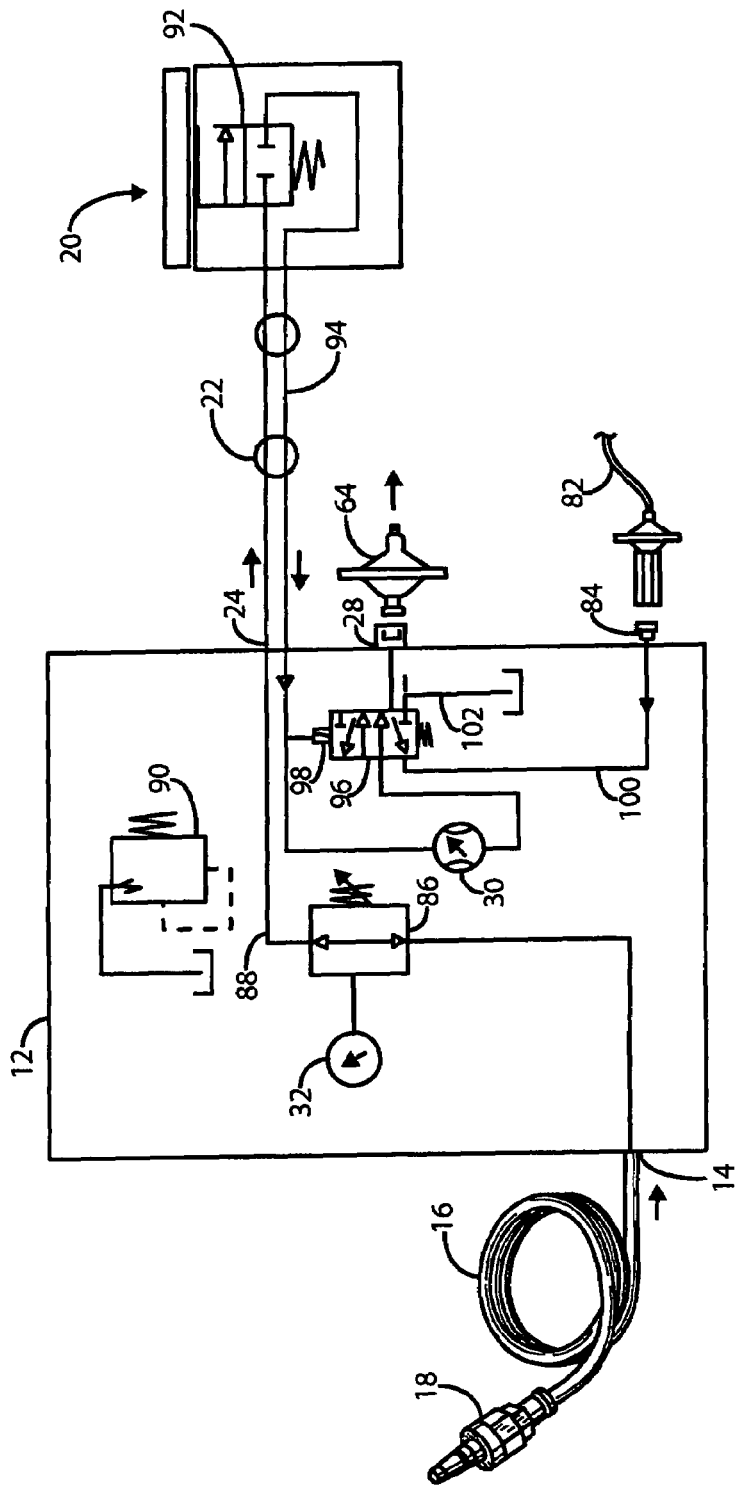
FIG. 5 is a schematic pneumatic diagram of the regulator module illustrated in FIG. 1.

Referring next to the schematic drawing of the regulator module illustrated in FIG. 5, a pressurized gas is applied to the input port 14 of the regulator assembly as already described and it is applied to a self-relieving pressure regulator 86 which is set at the factory to drop the pressure from the level applied to the gas inlet port 14, e.g. 200 psi, to a predetermined lower value, e.g., 20 psi. A gauge 32 is coupled to the regulator to provide a visual indication to a user that the pressure output from the regulator 86 is within prescribed limits.

The output from the regulator on line 88 is presented to a pressure limit safety valve 90 which functions to prevent gas pressure in the line 88 from exceeding a second predetermined level, e.g., 25 psi, in the event that the self-relieving pressure regulator 86 should fail.

Line 88 also leads to a two-way valve 92 contained within the foot switch assembly 20. Manual actuation of the foot switch opens the valve 92 permitting gas flow through the return line 94 to which a pilot-actuated, two-position, five-way pneumatic valve 96 is connected. When the pilot valve 98 senses pressure in the line 94 occasioned by the opening of the valve 92, the gas first flows through a flow meter 30 and then through the valve 96 to the gas outlet port 28.

As earlier mentioned, the flow of gas through the gas outlet port 28 is typically about 1-2 liters/minute and is filtered by a 0.2 micron filter unit 64 and then flows through the tubing 62 to the lumen 59 in the hub 58. At the same time that the footswitch 20 is depressed to produce this gas flow, the medical professional involved will slowly depress the plungers on the syringes 42 and 44 simultaneously to thereby flow the two non-homogeneous liquids (fibrin and thrombin) contained within the syringes down through the lumens of the elongated tubes 36 causing the two liquids to blend with the pressurized air flowing down the sheath 46 in the replaceable spray tip 66 and exit as an aerosol that can be directed against target tissue within the patient's abdominal cavity.

As those skilled in the art appreciate, during laparoscopic surgery it is common practice to insufflate the abdominal cavity to thereby move the abdominal wall away from internal organs on which the surgical procedure is being directed. The insufflation pressure is typically about 15 mmHg. In order to avoid a pressure increase due to the introduction of the gas through the spray set, the trocar 74 (FIG. 4) used in combination with the spray set of the present invention includes a vent port 78 that is in fluid communication with the interior of the abdominal cavity via a lumen in the trocar 74. A length of plastic tubing 82 connects to the vent port 78 of the trocar to the vent gas inlet port 84 of the regulator module 12 by way of a 0.5 micron filter in the vent line. So long as the footswitch 20 is depressed to open the control valve 92. The valve 96 also opens to apply the gas to the spray set. The pilot-controlled, pneumatic valve 96 simultaneously opens a path, including lines 100 and 102, to thereby flow the vented gas at a rate of 1-2 liters/minute to the atmosphere. With this arrangement, the same amount of gas introduced into the abdominal cavity due to the application of the spray of tissue adhesive is simultaneously exhausted, preventing a buildup of pressure within the abdominal cavity. The two sides of the valve 96 are mechanically interlocked to prevent one line from opening without the other. The vent line is normally closed to minimize insufflator gas usage when the footswitch is not depressed.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. Apparatus for mixing and administering two non-homogeneous liquids to target tissue in an endoscopic procedure, comprising:

(a) a spray set comprising two syringes for containing first and second non-homogeneous liquids, the two syringes adapted to be removably coupled to an applicator, said applicator including a pair of elongated tubes, each having a proximal end for attachment to the two syringes and a distal end, the pair of elongated tubes contained within a tubular sheath having a proximal end, a distal end and lumen in which the pair of elongated tubes are disposed and with a replaceable spray tip attachable to the distal end of the sheath and a gas inlet port at the proximal end of the sheath in fluid communication with the lumen thereof; and (b) a regulator module having a regulator input port adapted for connection to a source of gas under pressure, a gas outlet port adapted for connection to the gas inlet port of the sheath and a vent gas inlet port adapted for connection to a vent port of an endoscopic cannula, the regulator module being operative to vent a quantity of gas from the endoscopic cannula to the atmosphere, the quantity of vented gas being approximately equal to a quantity of gas introduced through the gas inlet port of the sheath; a pneumatic control valve coupled to the regulator for selectively permitting and preventing flow gas from the regulator input port to the gas inlet port of the sheath; a pilot-controlled, two-position, five-way pneumatic valve coupled in circuit with the pneumatic control valve for simultaneously turning on a flow of gas to the gas inlet port at the proximal end of the sheath and flowing gas from the vent port of the endoscopic cannula to the atmosphere.

2. The apparatus as in claim 1 wherein the pneumatic control valve is manually actuable.

3. The apparatus as in claim 1 and further including a self-relieving pressure regulator in the regulator module being in fluid communication with the regulator input port and the pneumatic control valve for limiting air pressure flowing to the pneumatic control valve to a first predetermined pressure less than that at the regulator input port.

4. The apparatus as in claim 3 and further including a pressure limit safety valve connected to a line leading to the pneumatic control valve for preventing gas pressure in said line from exceeding a second predetermined level in the event the self-relieving pressure regulator should fail.

5. The apparatus as in claim 1 wherein the pair of elongated tubes has differing lumen diameters.

6. The apparatus as in claim 1 wherein the spray set includes a Luer lock joined to the proximal ends of the pair of elongated tubes for coupling the two syringes individually to the pair of tubes.

7. The apparatus as in claim 6 and further including a hub member affixed proximate the proximal end of the sheath, the hub member including said gas inlet port.

8. The apparatus as in claim 6 wherein the Luer locks are joined to the proximal ends of the pair of elongated tubes by a pair of check valves.

9. The apparatus of claim 1 and further including a biohazardous gas filter coupled in series with the vent gas inlet port of the regulator module.

10. The apparatus as in claim 1 wherein the distal ends of the pair of elongated tubes extend out from the distal end of the tubular sheath.

11. An apparatus for mixing and administering bio-materials to target tissue in an endoscopic procedure, the apparatus comprising:
 an applicator comprising:
  a sheath having a lumen extending between a proximal end and a distal end;
  a gas inlet port at the proximal end of the sheath, the gas inlet port being in fluid communication with the lumen;
  a first elongated tube deposed within the lumen and adapted for fluid communication with a first syringe at the proximal end of the sheath; and
  a second elongated tube deposed within the lumen and adapted for fluid communication with a second syringe at the proximal end of the sheath; and
 a regulator module comprising:
  a regulator input port adapted for connection to a source of gas under pressure;
  a gas outlet port adapted for connection to the gas inlet port of the applicator; and
  a vent gas inlet port adapted for connection to a vent port of an endoscopic cannula, wherein the regulator module is operative to vent gas from the endoscopic cannula to the atmosphere at a volumetric flow rate that is approximately equal to a volumetric flow rate of gas introduced through the gas inlet port of the applicator;
  a pneumatic control valve coupled to the regulator module and adapted to control the flow of gas from the regulator input port to the gas inlet port of the applicator; a pilot-controlled, two-position, five-way pneumatic valve coupled in circuit with the pneumatic control valve for simultaneously turning on a flow of gas to the gas inlet port at the proximal end of the sheath and flowing gas from the vent port of the endoscopic cannula to the atmosphere.

12. The apparatus as in claim 11, wherein the regulator module further comprises a self-relieving pressure regulator in fluid communication with the regulator input port and the pneumatic control valve for limiting air pressure flowing to the pneumatic control valve to a first predetermined pressure less than that at the regulator input port.

13. The apparatus as in claim 11, wherein the first elongated tube and the second elongated tube each extend out from the distal end of the sheath.

14. The apparatus of claim 11, wherein the applicator further comprises a spray tip attachable to the distal end of the sheath.

15. The apparatus as in claim 11, and further comprising the first syringe and the second syringe, the first and second syringes containing the bio-materials.

16. The apparatus as in claim 15, wherein the bio-materials comprise fibrinogen and thrombin.

* * * * *